United States Patent [19]

Hennessy et al.

[11] 4,035,277
[45] July 12, 1977

[54] OXYGEN PROBE

[75] Inventors: Daniel R. Hennessy; David M. Pierre; Horace Pops, all of Fort Wayne, Ind.

[73] Assignee: Essex Group, Inc., Fort Wayne, Ind.

[21] Appl. No.: 723,355

[22] Filed: Sept. 15, 1976

[51] Int. Cl.² .................................... G01N 27/46
[52] U.S. Cl. ........................................ 204/195 S
[58] Field of Search ............ 204/195 S, 1 S; 324/29

[56]  References Cited
U.S. PATENT DOCUMENTS 3,772,177  11/1973  Rittiger et al. ................. 204/195 S

FOREIGN PATENT DOCUMENTS 1,283,712  8/1972  United Kingdom ............ 204/195 S Primary Examiner—G. L. Kaplan
Attorney, Agent, or Firm—Lawrence E. Freiburger; Robert D. Sommer

[57] ABSTRACT

A probe for measuring the oxygen content in a fluid, particularly a molten metal, by galvanic action. The probe assembly of the invention utilizes the thermal expansive properties of the probe components to increase the physical contact pressure between the solid electrolyte and its reference electrode so as to increase its reliability, ruggedness and lifetime.

5 Claims, 4 Drawing Figures

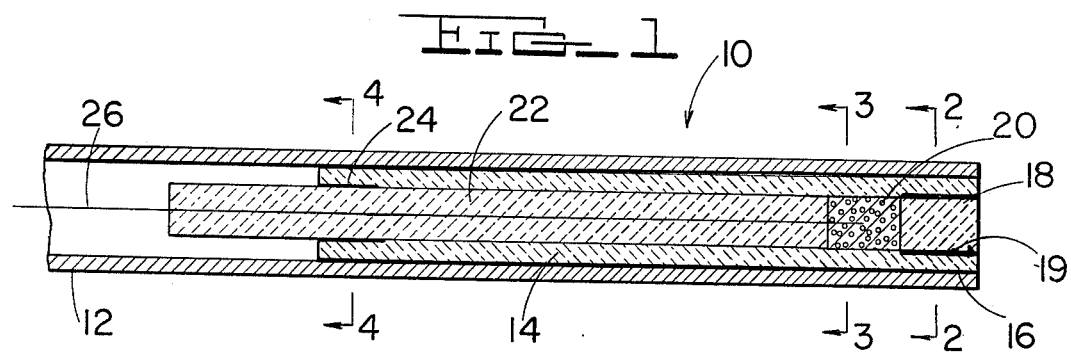
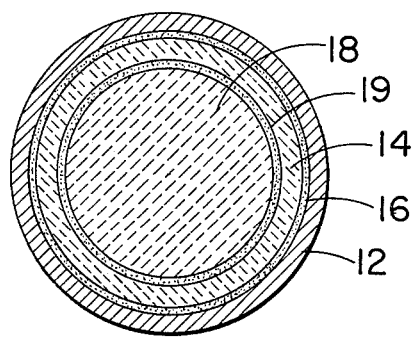
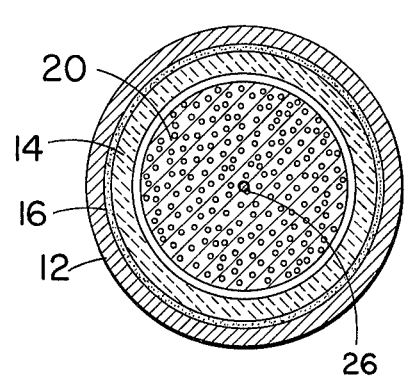
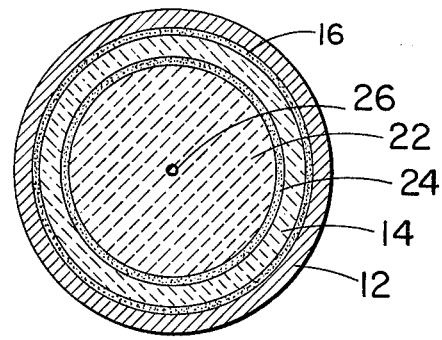

OXYGEN PROBE

BACKGROUND OF THE INVENTION

Oxygen probes which are essentially galvanic cells and which are adapted to measure the oxygen content in a molten metal are well known. However, all the prior art oxygen probes have suffered from one drawback which remains as a problem, namely the ability of the probe components to maintain the required electrical contact between the solid electrolyte and its electrode throughout a reasonable lifetime. As a result, the lifetime of prior art probes was much less than desired.

In order to overcome the difficulties encountered with prior art oxygen probes, the probe shown in U.S. Pat. No. 3,772,177 developed. The probe shown in this patent provides increased contact pressure between the solid electrolyte and the reference electrode by utilizing the thermal expansive properties of the contact rod.

While the probe disclosed in U.S. Pat. No. 3,772,177 operates satisfactorily, in many respects, for intended purpose, a more reliable rugged probe structure with increased lifetime is desired.

SUMMARY OF THE INVENTION

Accordingly, it is an object of the present invention to provide a more reliable and rugged probe structure than prior art probes. Additional objects and advantages of the present invention will become apparent as the description of the invention proceeds.

In summary, the probe structure of the present invention takes advantage of the dissimilar thermal expansion properties of certain of the probe materials to provide increased contact pressure between the reference electrode and the solid electrolyte. In accordance with the present invention, the reference electrode and the solid electrolyte pellet are axially aligned in abutting contact with one another and located in the end of a refractory tube with the electrolyte exposed to the fluid. A second refractory tube is located inside the first, is cemented thereto at its interior end, and is in abutting contact with the reference electrode. The second refractory tube is constructed of a different refractory material and performs a twofold purpose, namely, to urge the reference electrode toward the electrolyte with increasing temperature and to insulate a lead wire extending axially therethrough to the reference electrode from the outer stainless steel case.

BRIEF DESCRIPTION OF THE DRAWINGS

During the Detailed Description of the invention, reference will be made to the drawings, in which:

FIG. 1 is a longitudinal cross sectional view of the probe of the present invention;

FIG. 2 is a cross sectional view taken along line 2—2 of FIG. 1;

FIG. 3 is a cross sectional view taken along line 3—3 of FIG. 1; and

FIG. 4 is a cross sectional view taken along line 4—4 of FIG. 1.

DETAILED DESCRIPTION OF THE INVENTION

Referring now to the drawings where the preferred probe structure of the invention is disclosed such a probe generally indicated by reference numeral 10 may be enclosed in a tubular metal sheath 12 which serves to protect and house the probe. Since the disclosed probe is used to detect the oxygen in molten copper, the tube 12 is preferably constructed of grade 446 ferritic stainless steel since it does not readily dissolve in molten copper. It will be understood by those skilled in the art that different materials may be substituted for tube 12 if the probe is to be used in different metals.

A first refractory tube 14 is located coaxially in the end of tube 12 and is held in place by a layer 16 refractory cement. A solid electrolyte 18 is cemented at 19 inside refractory tube 14 flush with end thereof and a reference electrode 20 is located coaxially inside refractory tube 14 in axial alignment with the electrolyte 18 but is not cemented in place. Also located inside refractory tube 14 and in axial alignment with reference electrode 20 is a second refractory tube 22 which is attached to tube 14 only at the interior end by a layer of refractory cement 24. Finally a lead wire 26 extends axially through tube 22 and into reference electrode 20.

Generally speaking, the preferred materials for constructing the probe are conventional materials that are readily available. For example, the solid electrolyte 18 may be a zirconium oxide which has been stabilized with calcium oxide; the reference electrode 20 may be an approximate mixture 50% of Molybdenum and 50% Molybdenum Oxide by weight which has been pressed into pellet form; refractory tube 22 may be an alumina refractory and refractory tube 14 may be a mullite refractory.

The inventive feature of the present invention lies in the selection of the proper refractory materials or tubes 14 and 22. In accordance with the present invention, tubes 14 and 22 are chosen of different refractory materials having dissimilar coefficients of thermal expansion so that, at the temperature of use, the expansion of tubes 14 and 22 due to heating urges electrode 20 into more intimate contact with the solid electrolyte 18. The refractory tube 22 also advantageously serves the purpose of holding lead wire 26 in place so as to insulate it from the outer metal tubing 12.

The operation of the oxygen probe is well known in the art. Therefore, its operation will not be described in detail. It should suffice to say that whenever such a probe is immersed in molten copper and brought to temperature an EMF is created across the leadwire 26 and the molten copper which is proportional to the oxygen content in the copper.

By way of example, the probe shown in the drawing FIGURES was constructed in the following manner from the indicated materials as follows;

First, the reference electrode is formed from an approximate mixture by weight of 50% Molybdenum powder and 50% Molybdenum Dioxide by pressing under approximately 8000 pounds force in a one quarter inch die for 15 seconds. The chromel lead wire 26 is inserted into the Mo—Mo° 2 mixture prior to pressing. The formed pellet is then sintered in an argon atmosphere at 2200° F over-night.

The solid electrolyte may be a 7½% Calcia stabilized ¼ inch diameter Zirconia rod available from Zirconium Corporation of America of Solon, Ohio, which is cut into pellets and fits inside refractory tube 14.

Refractory tube 14 may be cut from conventional mullite glass tubing which is ¼ inch in inner diameter and ⅜ inch outer diameter. Such material is available from McDanel Refractory, 519 Ninth Ave., Beaver Falls, Pa.

Refractory tube 22 may be a ¼ inch outer diameter alumina insulator likewise available from McDanel Refractory.

Finally, the cement used may be a refractory cement known as "UltraTemp 516" which is properly mixed and is available from AREMCO Products, Ossining, N.Y., and the tubing 12 may be a 446 grade ferritic stainless steel tubing.

In assembling the probe, care should be taken that the cement is applied only at the indicated places and that the assembly is air dried overnight and then cured as follows:

1. Heat probe slowly to 200° F in air and hold for 18 20 hours.
2. Then increase temperature slowly to 250° F and hold for 1 hour.
3. Then increase temperature slowly to 1100° F over 2 hours.
4. Cool slowly to less than 200° F.

It has been discovered that the above-described probe structure results in a superior electrical contact between the electrode and electrolyte because the different thermal expansion of the mullite and alumina tubes tends to urge the reference electrode into more intimate contact with the electrolyte. For example, the alumina tube 22 at 1000° C has a thermal expansion coefficient per ° C of $8.1 \times 10^{-6}$, and the mullite tube of the preferred embodiment has a thermal expansion coefficient per ° C at 1000° C of around $5.0 \times 10^{-6}$. By referring to FIG. 1, it will be seen that the alumina refractory tube 22 will expand to a greater degree than the mullite refractory tube 14, resulting in a new movement of tube 22 to the right as viewed in FIG. 1 so as to increase the contact pressure between reference electrode 20 and electrolyte 18.

While the preferred embodiment of the invention has been described for purposes of illustration, obvious modifications will occur to those skilled in the art. Accordingly, it is intended that the invention be defined in the appended claims.

What is claimed is:

1. An oxygen probe of the galvanic cell type for determining the oxygen content of a high temperature molten metal comprising:
    an open protective, tubular member;
    a second tubular member located coaxially inside one end of said open tubular member and cemented thereto;
    a solid electrolyte pellet and a reference electrode pellet axially abutting one another and located coaxially inside the end of said second tubular member, said solid electrolyte pellet being exposed to the open end of said open tubular member and further being cemented to said second tubular member;
    a third tubular member located coaxially inside said second tubular member in axial abutting contact with said electrode pellet, said third tubular member being cemented to said second tubular member at the end opposite said electrode and having a greater coefficient of thermal expansion than said second tubular member so that the relative thermal expansion of said second and third tubular members increases the abutting contact between said electrode and said solid electrolyte pellet; and
    means for making an electrical connection to said reference electrode.

2. The oxygen probe claimed in claim 1, wherein said second tubular member is constructed of a mullite refractory and said third tubular member is constructed of an alumina refractory.

3. The oxygen probe as claimed in claim 1, wherein the thermal expansion coefficient of said second tubular member per ° C at 1000° C is approximately $5.0 \times 10^{-6}$.

4. The oxygen probe as claimed in claim 1, wherein the thermal expansion coefficient of said third tubular member per ° C at 1000° C is approximately $8.1 \times 10^{-6}$.

5. The oxygen probe as claimed in claim 1, wherein said open protective tubular member is a stainless steel tube, and said means for making an electrical connection to said reference electrode comprises a lead wire extending axially through said third tubular member.

* * * * *